US006931352B2

(12) United States Patent
Cryer et al.

(10) Patent No.: US 6,931,352 B2
(45) Date of Patent: Aug. 16, 2005

(54) SYSTEM AND METHOD FOR MONITORING THE CONDITION OF A HEAT EXCHANGE UNIT

(75) Inventors: Robert Douglas Cryer, Erie, PA (US); Charles Joseph Waugaman, New Wilmington, PA (US); Lance Thomas Stewart, Grove City, PA (US); Dario Patrico Escobar, Erie, PA (US); Manoj P. Kumar, Bangalore (IN); Laurence Richard Handler, Erie, PA (US); Cecil M. Daniel, Erie, PA (US)

(73) Assignee: General Electric Company

( * ) Notice: Subject to any disclaimer, the term of this patent is extended or adjusted under 35 U.S.C. 154(b) by 476 days.

(21) Appl. No.: 10/271,514

(22) Filed: Oct. 16, 2002

(65) Prior Publication Data

US 2003/0075314 A1 Apr. 24, 2003

Related U.S. Application Data

(60) Provisional application No. 60/343,843, filed on Oct. 19, 2001.

(51) Int. Cl.⁷ .................................................. G06F 11/30
(52) U.S. Cl. ....................................... 702/182; 702/130
(58) Field of Search .......................... 62/126, 127, 129; 73/112, 865.9; 165/1, 11.1, 41, 42, 299; 374/10, 43, 210; 701/99, 102; 702/33, 34, 35, 81, 84, 127, 130, 132, 182, 183, 189

(56) References Cited

U.S. PATENT DOCUMENTS

| | | | | |
|---|---|---|---|---|
| 4,316,251 A | * | 2/1982 | Saito et al. ................... 701/36 |
| 4,381,549 A | * | 4/1983 | Stamp et al. .................. 62/126 |
| 4,390,058 A | | 6/1983 | Otake et al. |
| 4,761,967 A | * | 8/1988 | Sumikawa et al. ............ 62/201 |
| 4,766,553 A | | 8/1988 | Kaya et al. |
| 5,149,025 A | | 9/1992 | Utterback et al. |
| 5,152,335 A | * | 10/1992 | Doi et al. ..................... 165/204 |
| 5,181,389 A | * | 1/1993 | Hanson et al. ................. 62/126 |
| 5,353,653 A | * | 10/1994 | Watanabe et al. ........... 73/865.9 |
| 5,392,716 A | | 2/1995 | Orschek et al. |
| 5,446,452 A | | 8/1995 | Litton |
| 5,615,733 A | * | 4/1997 | Yang .......................... 165/11.1 |
| 6,178,928 B1 | * | 1/2001 | Corriveau ................. 123/41.12 |
| 6,225,907 B1 | * | 5/2001 | Derryberry et al. .......... 340/584 |
| 6,241,383 B1 | * | 6/2001 | Feller et al. ................... 374/40 |
| 6,678,628 B2 | * | 6/2001 | Ryan et al. .................. 702/132 |

* cited by examiner

*Primary Examiner*—Michael Nghiem
*Assistant Examiner*—Douglas N Washburn
(74) *Attorney, Agent, or Firm*—Carl Rowold, Esq.; Robert L. Wolter, Esq.; Beusse, Brownlee, Wolter, Mora & Maire, P.A.

(57) ABSTRACT

A system and method for monitoring the effectiveness of a heat exchange unit, which comprises at least one or more sensors for taking a plurality of temperature readings of a heated fluid, a coolant and fluids passing through the heat exchange unit. The temperature readings are transmitted and/or entered into a processor capable of comparing the temperature readings and calculating a measure of effectiveness of the heat exchange unit. The processor is in communication with a database that maintains at least one predetermined parameter limit associated with the effectiveness of the heat exchange unit. The processor analyzes the data and is also capable of generating a signal indicative of the health or condition of the heat exchange unit.

26 Claims, 4 Drawing Sheets

SYSTEM AND METHOD FOR MONITORING THE CONDITION OF A HEAT EXCHANGE UNIT

Applicant herein claims priority to the Provisional Patent Application, U.S. Ser. No. 60/343,843, filed on Oct. 19, 2001.

BACKGROUND OF THE INVENTION

The present invention relates generally to systems and methods for the condition-based monitoring of machines. More specifically, the present invention pertains to monitoring the condition of heat exchange units.

In conducting a condition-based maintenance (CBM) program for machines, or components of machines, analysts using physical evaluation and a knowledge base, can make a decision on the relative health of various components of the machine, or the machine itself. Typically, sensors are mounted at various locations on a machine to detect at least one, or more, physical phenomenon that is produced by the operation of the machine. The detection and analysis of the phenomena is ideally performed in-situ in order to provide a real-time analysis of the condition of the machine or component of the machine.

For example, vibrations emanating from the operation of a bearing assembly are detected using an accelerometer placed in proximity to the bearing. The vibrations of the bearing assembly produce a vibrational energy that is measurable in amplitude and frequency. Data obtained during the operation of the bearing assembly is compared to data stored within a database that usually includes a plurality of parameters relative to the operation of the bearing assembly. The parameter limit data is obtained from an analysis of the bearing assembly. An analyst assesses the condition of the bearing assembly by comparing the operational data of the bearing assembly to the stored parameter data.

Other physical phenomena such as sound or temperature may also be detected and analyzed for condition based monitoring of a machine. For example, the temperature and flow rate of fluid media in a heat exchanger may be analyzed for determining the health of the heat exchange unit. A heat exchanger performance monitor is disclosed in U.S. Pat. No. 4,766,553 (hereinafter referred to as the "'553 Patent"). The system of the '553 Patent discloses the use of temperature transmitters mounted to an evaporator or condenser, which are electronically linked to software programmed to input temperature readings into equations for analysis of the performance of the heat exchanger.

At least with respect to mobile assets, such as locomotives, automated CBM has not been utilized for assessing the health of a heat-exchange unit. The monitoring of a heat exchange unit typically includes a subjective analysis of the temperature output of the exchange unit, which may lead to inconsistent results from analyzer to analyzer. In the operation of similar machine assets, such as in the operation of a fleet of mobile assets subject to a condition based monitoring system, the generation of parameter threshold requirements for individual heat exchange units may not be practical. In addition, condition-based monitoring of stationary heat exchange units does not factor changing ambient environmental conditions into the analysis of the health of a unit.

With respect to locomotives, non-contact infrared temperature sensors have been used to take temperature readings of components of a locomotive. Specifically, infrared sensors have been mounted subjacent a railroad track at locomotive service stations. When the locomotive is stopped for servicing at a station, the infrared sensors are activated and detect the temperature of bearing assemblies of the locomotive wheel casings. However, such sensors may not be practically installed for operation with internal components of some machines. Indeed, some internal operating components cannot be practically analyzed using conventional stationary contact or non-contact sensors.

BRIEF SUMMARY OF THE INVENTION

Accordingly, a system and method are described herein for the monitoring the condition of a heat exchange unit having a first fluid and a second fluid passing through the heat exchange unit. The second fluid is a coolant for lowering an elevated temperature of the first fluid by heat exchange.

The system comprises at least one sensor for taking temperature readings representative of temperatures of the first fluid and/or the second fluid. The temperature readings may include at least two temperatures associated with either the first fluid or at least two temperatures associated with the second fluid. In an exemplary embodiment, the sensor is a portable non-contact infrared sensor, which is hand-held by a technician for taking the temperature readings. The sensor is held in spaced relation to a plurality of discrete points along the surface of the heat exchange unit to take the temperature readings.

The system is also equipped with a processor, in communication with the sensor, in which data representative of the temperature readings is entered. A database, in communication with the processor, comprises data that is representative of at least one predetermined condemning limit associated with a measure effectiveness of the heat exchange unit. The condemning limit data associated with the effectiveness of the heat exchange unit is obtained from an analysis of a population of like heat exchange units. Particularly in the operation and maintenance of a fleet of mobile assets, component parts such as the heat exchange unit are purchased from the same manufacturer. The units are manufactured from the same materials and specification, so data gathered from the population of units is analyzed to identify parameter limits.

The processor is programmed to calculate a measure effectiveness of the heat exchange unit by comparing the data representative of the temperature readings. In addition, the processor compares the measure of effectiveness of the heat exchanger to the predetermined condemning limit, stored in the database, and associated with the effectiveness of the heat exchange unit for the population of like units. The processor then generates a signal indicative of the condition of the heat exchange unit.

In operation, the sensor is positioned proximal to the heat exchange unit to take temperature readings of the first fluid or second fluid. In a preferred method of operation, the surface temperatures comprise an inlet surface temperature for the first fluid entering the unit and an outlet surface temperature for the first fluid exiting the unit. In addition, an outlet surface temperature for the second fluid exiting the heat exchange unit is taken. The limits associated with the effectiveness of the heat exchange unit and the processor generate a signal that is indicative of a condition of the heat exchange unit.

In addition to the above-described condemning limit related to the effectiveness of a heat exchange unit, the database may also contain data representative of one or more operating parameters of the heat exchange unit and/or the vehicle in the case of analyzing mobile assets. In such an embodiment, the database may contain at least one measure of effectiveness obtained from analyzing the like population; and the measure of effectiveness is associated with one or more operating parameters of the heat exchange unit, including, but not limited to ambient temperature, geographic location of a mobile asset, and elevation/altitude of the mobile asset, humidity, barometric pressure, and the time period within a calendar year. An additional sensor may be used to detect a level of at least one of the operating parameters of the heat exchange unit. In operation, the system detects the operating parameters of the heat exchange unit, and identifies the corresponding predetermined condemning limit associated with the operating parameter. The measure of effectiveness is then compared to the predetermined condemning limit to determine a condition of the heat exchange unit.

The system and method of the present invention is particularly advantageous because a technician having minimum skill level or training can operate the invention. The present invention also provides immediate feedback relative to the condition of the heat exchange unit. The processor is programmed to automatically calculate the measure of effectiveness. A technician simply takes the temperature readings necessary for the calculation and enters the readings into the processor along with the other operating parameter concerning, for example, ambient conditions and/or predetermined time periods associated with the operation of the heat exchange unit. The processor performs an algorithmic function and generates the signal concerning the condition of the heat exchange unit.

DETAILED DESCRIPTION OF THE INVENTION

The present invention for a system and method for monitoring a condition of a heat exchange unit preferably utilizes non-intrusive, non-contact temperature sensors to take at least one surface temperature reading of the heat exchange unit to determine the health of the heat exchange unit.

The present invention in some instances may be described in the context of the environment of the operation of an internal combustion engine for motor vehicles. Such heat exchange units may be commonly referred to as "intercoolers;" however, the present invention is not limited to an intercooler, but may be used with any heat exchange unit such as condensers, evaporators, boilers, air coolers or pre-coolers, or other devices having heat transfer surfaces. However, the present invention may also utilize contact sensors mounted in proximity to the unit or probe the fluid to take a direct temperature reading of the first fluid and/or second fluid.

Figure 1:
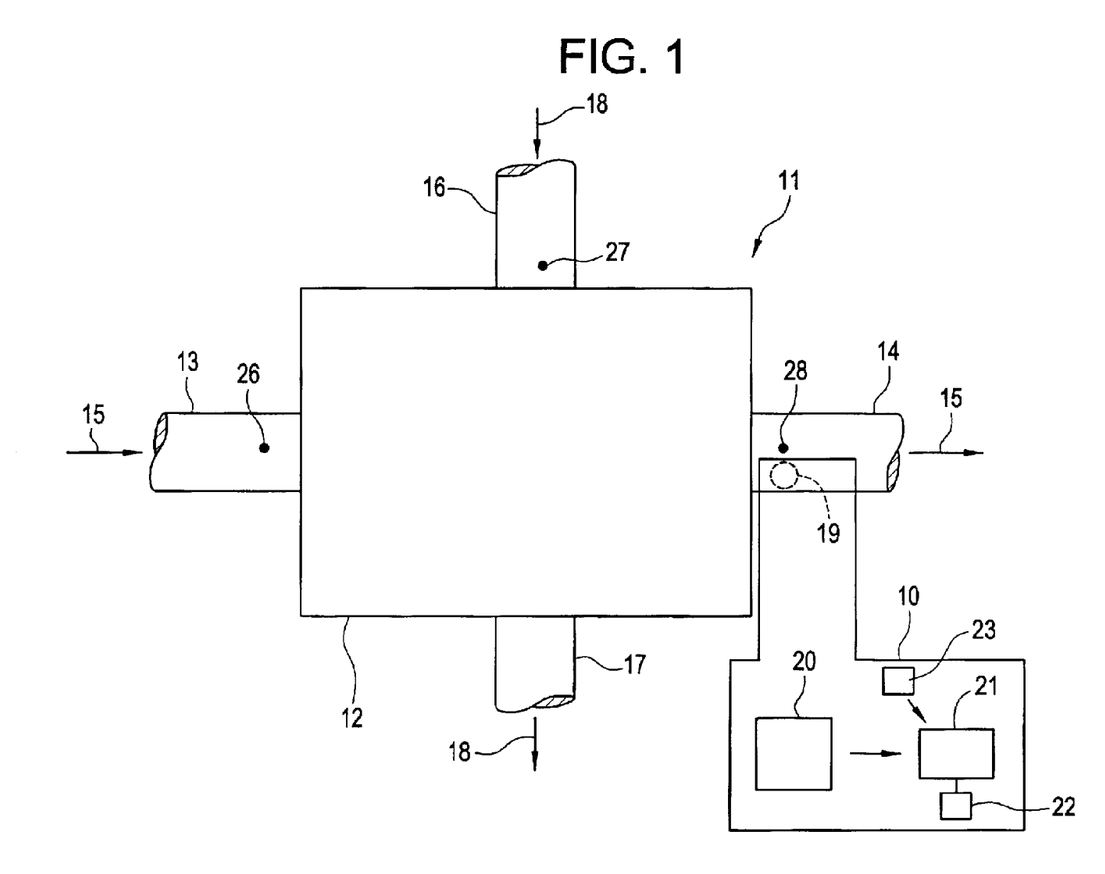
FIG. 1 is a schematic of a heat exchange unit incorporating the present system for monitoring the condition of a heat exchange unit.

With respect to FIG. 1, a schematic illustrates the system 10 in conjunction with a heat exchange unit 11. The heat exchange unit 11 generally includes a heat or energy exchange chamber 12, through which a first fluid 15 and second fluid 18 flow. The first fluid 15 enters the chamber 12 at an elevated temperature as a result of the operation of a machine. For example, with respect to a turbo-charged internal combustion engine, air discharged from the turbo charger is heated and must be cooled prior to recirculation to the turbo charger. Water maintained within the engine cooler system is directed through the chamber 12, via conduits to cool the discharged air.

The first fluid 15 enters the chamber 12 via first inlet tube 13, and is discharged from the chamber 12 via the first outlet tube 14. A second fluid 18, or coolant, enters the chamber 12 via a second inlet tube 16, and exits the chamber 12 via the outlet tube 17. The second fluid 18 enters the chamber having a temperature lower than the elevated temperature of the first fluid 15. As the first fluid 15 and second fluid 18 pass through the chamber 12, heat exchange occurs between the first fluid 15 and second fluid 18, whereby the first fluid is cooled to an acceptable operating temperature. The heat exchange between the two fluids takes place without physical contact between the fluids. Typically, the first fluid 15 and/or second fluid 16 pass through a series of conduits or manifold systems within the chamber 12 to facilitate the heat exchange between the two fluids.

The system shown in FIG. 1 includes at least one sensor 20 for taking a plurality of temperature readings of the exterior surface of the heat exchange unit 12, and a processor 21 for analyzing the temperature readings to determine the condition or health of the heat exchange unit 11. In an exemplary embodiment, the sensor 20 is a hand-held portable infrared non-contact thermometer. One may maneuver such sensors to different positions with respect to the heat exchange unit 11 in order to take a sufficient number of temperature readings to analyze the health of the heat exchange unit 11. Infrared guns or infrared thermography cameras are available from a variety of manufacturers or distributors including Raytek Inc., Image Systems, Inc., Grainger Inc. or Flir Systems, Inc.

The system 11 may also be equipped with one or more additional sensors or monitors 23, as shown in FIG. 1, to detect operating parameters that may influence the operation of the heat exchange unit 11, which will be described in more detail below. The type of sensor 23 used will depend on the specific operating parameter to be detected. For example, a thermometer may be used for detecting an ambient temperature, or a GPS (global positioning satellite) unit may be used for determining a geographic location of the heat exchange unit.

The system 10 may also include at least one contact sensor 19 mounted in one of tubes 13, 15, 16 and 17 to take a direct temperature reading of the first fluid 15 and second fluid 16. Such sensors 19 are known to those skilled in the art of conditioned based monitoring systems. The sensor 19 is preferably linked to a data access area for downloading temperature readings from the sensor 19. The temperature reading of the sensor 19 is entered into the processor as described below.

The sensor 20 is positioned relative to a plurality of predetermined discrete points along the exterior surface of the unit 11. With respect to the above-described non-contact infrared sensors, the sensor 20 is positioned in spaced relation to the discrete points. An analysis of like heat exchange units should empirically determine the areas on the unit from which the temperature readings are taken. In operation, the sensor 20 is used to take temperature readings representative of the temperatures of the first fluid 15 and/or the second fluid 18 at the points from which the temperature readings are taken. The temperature readings are transmitted to the processor 21, which is capable of calculating a computation that is representative of the effectiveness of the heat exchange unit 11. The computation is expressed as a percentage of the effectiveness of the unit 11 on a scale of 0% to 100%.

The temperature readings may be manually entered into the processor, or the sensors 20 may be directly linked to the processor to automate the transmission and entry of the temperature readings. The processor 21 is programmed with an arithmetic equation to calculate a measure of effectiveness of the heat exchange unit 11 using the temperature readings of the exterior surface of the heat exchange unit 11. At least two temperatures associated with the first fluid 15 and/or two temperatures associated with the second fluid 18 are compared to one another to calculate the measure of effectiveness. In an exemplary embodiment, at least one temperature representative of the first fluid and at least one temperature reading representative of the temperature of the second fluid (or coolant) is taken for analysis. For example, a temperature (also referred to as an inlet temperature, or T1) representative of the first fluid entering the chamber 12 is taken; a temperature (also referred to as an outlet temperature or T2); and, a temperature associated with the second fluid entering the chamber 12 (also referred to as T3).

As mentioned above, the temperature readings, T1, T2 and T3, are measurements of the surface temperature of the heat exchange unit 11 taken at predetermined discrete points. An adjustment factor may be incorporated in the algorithm in order to accurately reflect the temperature readings of the first fluid 15 and second fluid 18, and/or the calculation of the effectiveness of the heat exchange unit 11. A sample algorithm for calculating the effectiveness computation of the heat exchange unit 11 may be characterized as a ratio of the change in the inlet temperature (T1) of the first fluid 15 and the outlet temperature (T2) of the first fluid, to the difference in the between inlet temperature (T2) of the first fluid and the inlet temperature (T3) of the second fluid. An equation representing the algorithm is listed below:

$$\left[\frac{(T1-T2)A}{(T1-T3)}\right]^{15} + B$$

where T1 is the inlet temperature of the first fluid;

T2 is the outlet temperature of the first fluid;

T3 is the inlet temperature of the second fluid; and,

A and B are the adjustment factors.

The adjustment factors A and B may include predetermined numeric constants that may be calculated using regression analysis of the temperature readings, T1, T2 and T3. The adjustment factors may be empirically calculated by comparing temperature readings taken from more precise contact sensors that directly measure the temperature of the fluids, and the temperature readings of the exterior surface of the heat exchange unit 11. The adjustment factors are preferably determined from a population of like, or similar, heat exchange units.

A database 22, in communication with the processor 21, contains at least one limit associated with the measure of effectiveness of the heat exchange unit 11. The limit may also be referred to as a condemning limit, in the sense that if the measure of effectiveness exceeds the condemning limit, a signal is generated that indicates a health of the unit. The predetermined limit data relative to measure of effectiveness of the heat exchange unit 11 is obtained from an analysis of a selected population of like heat exchange units.

Figure 2:
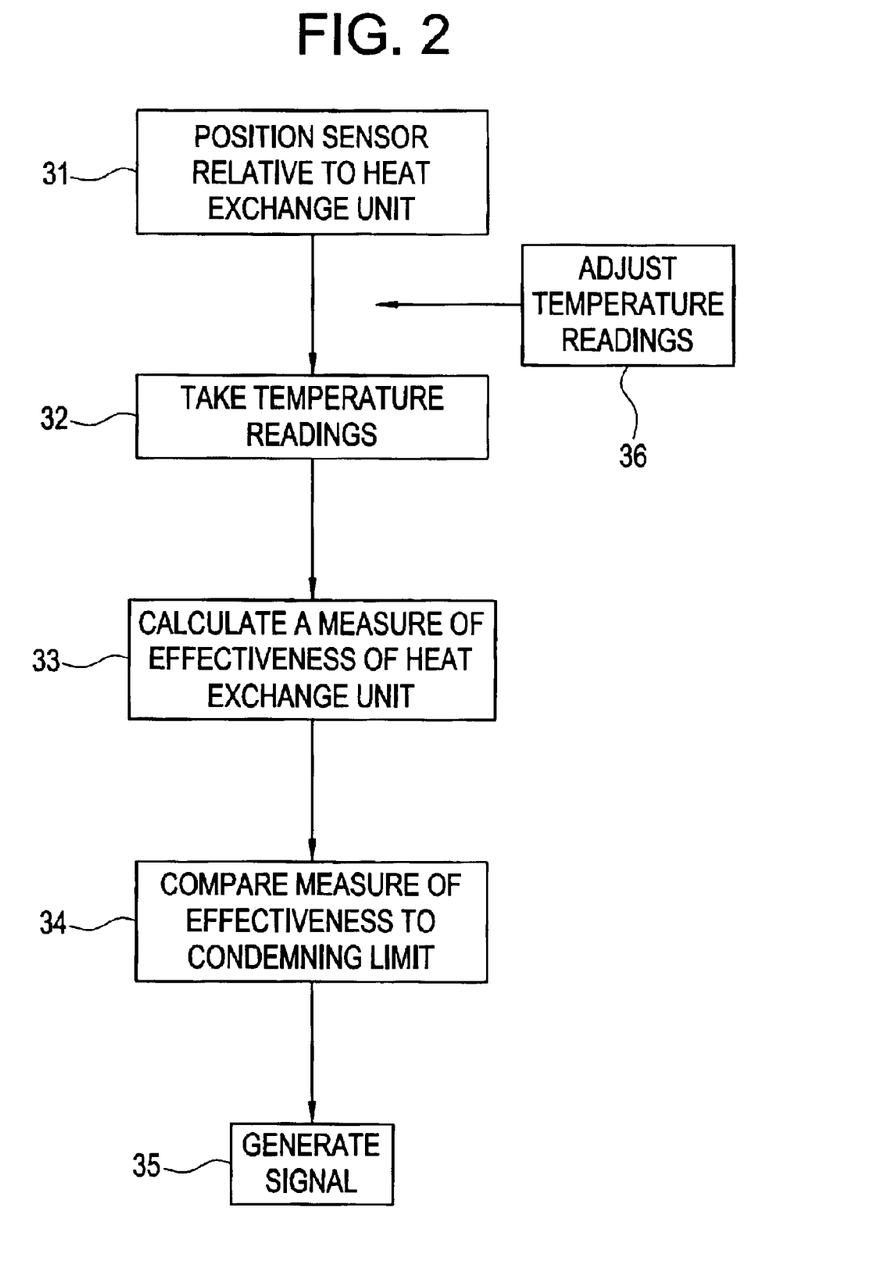
FIG. 2 is a flow chart describing the method for monitoring the condition of the heat exchange unit.

A method for the present invention is depicted in the flow charts in FIG. 2. With respect to Steps 31 and 32, the sensor 20 is positioned relative to a plurality of discrete points on the surface of the heat exchange unit 11. For example, with reference to FIG. 1, temperature readings may be taken at points 26 and 27, along the exterior surface of inlet tubes 13 and 16, respectively. A temperature reading may be taken at point 28 along the surface of the outlet tube 14. Similarly, contact or probe sensors may be positioned at the points 26, 27 and 28, to directly read the temperature of the fluids 15 and 18.

In Step 33, the temperature readings are then transmitted and/or entered into the processor 21, where the temperature readings are used to calculate the measure of effectiveness of the exchange unit 11. The measure of effectiveness of the exchange unit 11 is calculated as a percentage, from 0% to 100%, of the operating efficiency of the heat exchange unit 11. In an intermediate Step 36, or as a step combined with the calculation of effectiveness measurement, the temperature readings are adjusted using the adjustment factors (A and B referred to above) to reflect a temperature of the first fluid 15 and second fluid 18 at points 26, 27 and 28.

In Step 34, the measure of effectiveness, calculated in Step 33, is compared to the limits maintained in the database 22 in communication with the processor 21. The condemning limits are associated with the effectiveness of the heat exchange units and are obtained from an empirical analysis of a population of like heat exchange units. The limits may include at least one minimum condemning limit above which the heat exchange unit 11 effectively operates, and/or below which the heat exchange unit 11 requires maintenance, or at least an inspection.

With respect to Step 35, the processor generates a signal indicative of the condition of the heat exchange unit. For example, if the measure of effectiveness falls below the condemning limit, the processor may generate a warning signal that the heat exchange unit requires maintenance. The signal may take the form of a pass/fail response that leads to an inspection of the unit. In addition, the processor 21 and database 22 may maintain and generate multiple signals corresponding to different measures of effectiveness. For example, a percent effectiveness of 70% may generate a signal that requires inspection of the unit 11, while a percent effectiveness computation of 60% may generate a signal of impending failure of the unit 11, which must be replaced.

The database 22 may also include operating parameters associated with the operation of the heat exchange unit 11. For example, the operating parameters may include ambient environmental conditions that may influence the operation of the heat exchange unit 11, such as ambient temperature, and geographic location of the unit 11. In addition, the operating parameters may include predetermined time periods within a calendar year associated with the operation of the heat exchange unit 11 and the ambient environmental conditions.

These operating parameters may be especially useful for units 11 operating on mobile assets, such as locomotives that travel over extended time periods and distances and are subject to changing ambient environmental conditions. These ambient conditions directly affect the effectiveness of the heat exchange unit. The heat exchange unit 11 may operate less efficiently under elevated temperatures, which typically occur in the spring and summer months of April through August. That is to say, the heat exchange unit 11 must operate more efficiently during these warmer months in order to perform the same level of work at a less efficient level in cooler months. Accordingly, the condemning limits for the measure of effectiveness for the months of April through August will be higher than the limits corresponding to the remaining months of the year. In addition, the geographic location, including the elevation of the unit 11 may also be considered, so the database 22 is able to assess that a heat exchange unit operating during the month of May at 75° should operate at or above an efficiency level of 76%.

Figure 3:
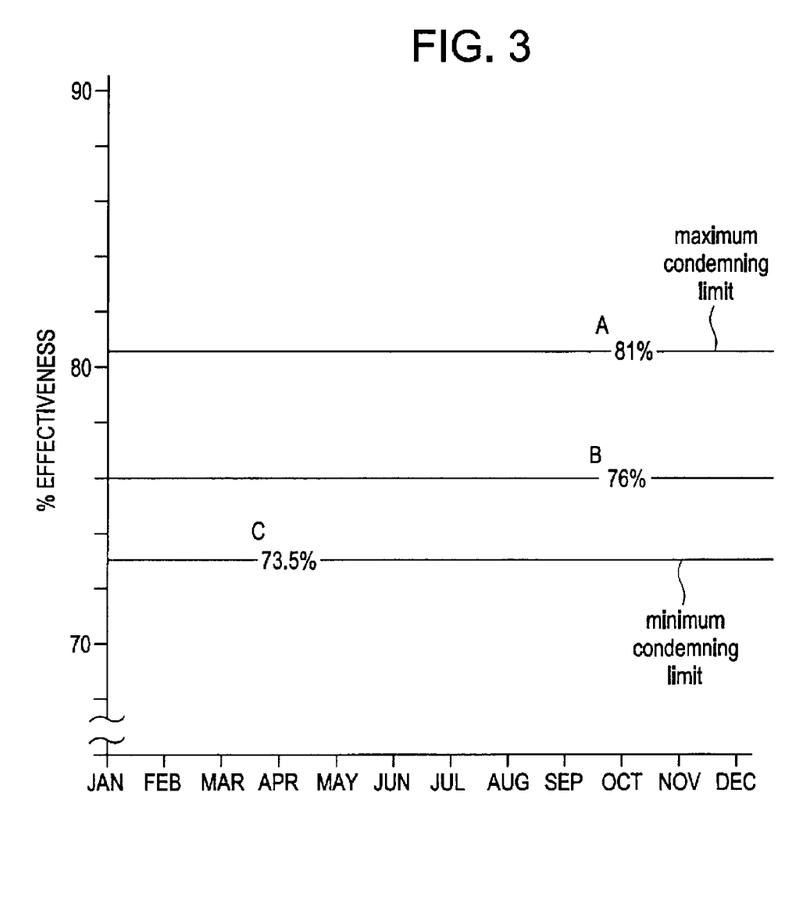
FIG. 3 is graph plotting the percent effectiveness parameter limits with respect to predetermined time periods of a calendar year.

By way of example, condemning limits corresponding to the effectiveness of the heat exchange unit 11 have been plotted on the graph shown in FIG. 3, with respect to operating parameters associated with the operation of the heat exchange unit 11. The percent effectiveness is plotted along the "y" or vertical axis, and the calendar months are plotted along the horizontal, or "x" axis. The graph includes a condemning limit A, B, and C for each of three different time periods of the year. The limit A for the months of February through March is 76%, the limit for the months of April through August is 81%, and the limit for the months of September through January is 73.5%.

During the winter and spring months of January through April, the temperatures of the condemning limits may be relaxed and the heat exchange unit 11 may be permitted to operate less efficiently without maintenance. If the percent effectiveness drops below 73.5% during the months, the processor 21 should generate a signal indicating that action is required. Similarly, the condemning limits A and B for the respective time periods serve as a minimum percent effectiveness above which the heat exchange unit must operate during the respective calendar time periods. In addition, the condemning limit C may serve as a minimum condemning limit. If the percent effectiveness falls below C (73.5%) at any time of the year, the processor should signal that action is necessary. The condemning limit A (81%) may similarly serve as a maximum limit, so that a measure of effectiveness equal to or greater than A, regardless of the time of year, will always result in a passing signal.

To the extent that the detected level of the operating parameter may not equal to or fall within given ranges of the operating parameter data, the processor may be programmed to adjust or normalize the measure of effectiveness relative to the difference in operating parameters. Similarly, the predetermined condemning limit may also be adjusted to account for a difference in the detected level of the operation parameters and the associated operating parameter data.

Figure 4:
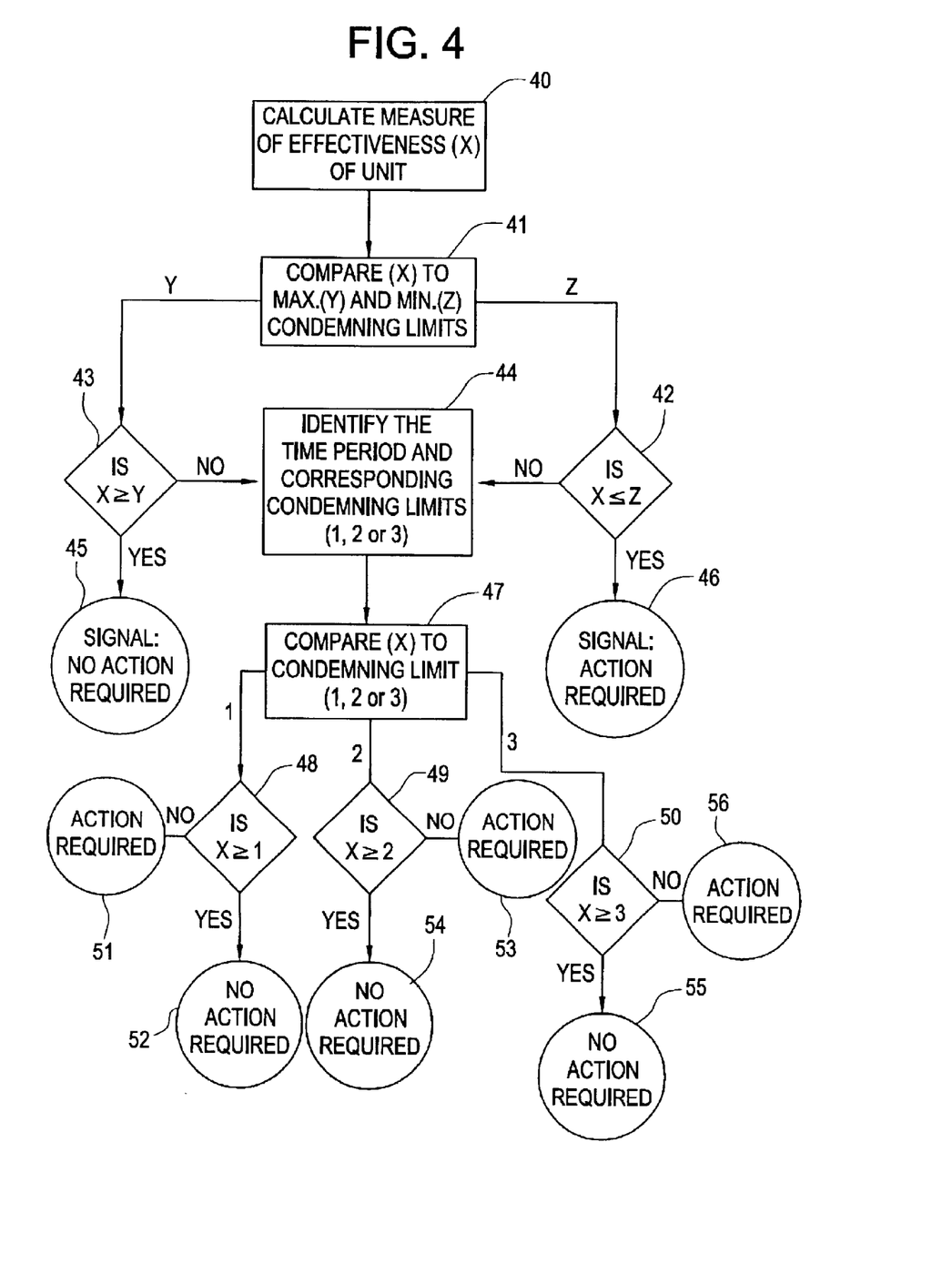
FIG. 4 is an algorithm that may be used in the system and method for monitoring the condition of the heat exchange unit.

With respect to FIG. 4, the processor may be programmed to follow the below-described algorithm incorporating steps for considering at least one operating parameter. After the measure of effectiveness computation, X, is calculated in step 41, it is compared to the maximum condemning limit, Y, and the minimum condemning limit, Z. If the measure of effectiveness X exceeds the maximum limit Y, then no action is required and a corresponding signal is generated, as shown in steps 43 and 45. Similarly, in steps 42 and 46, if the measure of effectiveness X is equal to or less than the minimum-condemning limit Z, then a signal corresponding to the necessary action required is generated.

If the measure of effectiveness X does not exceed the maximum X or minimum Y parameter limits, then step 44 is initiated to identify the time period of operation within the calendar year to the corresponding condemning limit 1, 2 or 3. A time period operating parameter is used by way of example. The foregoing description could also be described using such operating parameters as ambient temperature and geographic location of the heat exchange unit 11.

As shown in steps 47 through 55, depending on the time of year, the measure of effectiveness X will be compared to condemning limits 1, 2 or 3. If the measure effectiveness X is equal to or exceeds the respective condemning limits 1, 2 or 3 correspond to a predetermined time period, no action will be required. On the other hand, if the effectiveness computation X is equal to or less than the respective predetermined condemning limits 1, 2 or 3, a signal indicative of the necessary action is generated.

In addition to the foregoing algorithmic functions with respect to time periods and corresponding condemning limits, the above-identified operating parameters relative to the ambient environment may be incorporated into analysis of the computation of the measure of effectiveness. For example, the ambient temperature may be identified with each respective time period of the calendar year. A predetermined temperature, or range of temperatures, may correspond to at least one condemning limit. Accordingly, within a single predetermined time period, the database 22 may maintain a plurality of condemning limits, wherein each condemning limit corresponds to a predetermined temperature or temperature range. Alternatively, the processor and database 22 may be programmed to operate as a function of predetermined temperatures and corresponding condemning limits, without reference to the previously described time periods. Similarly, the algorithmic functions may also factor the geographic location of the unit 11, so that the condemning limit for the measure of effectiveness may be associated with the combination of location of the unit at a predetermined time period and operating at an ambient temperature. As one skilled in the art will appreciate, any combination of the operating parameters may be used to analyze the measure of effectiveness and assess the condition of the heat exchange unit 11.

While the invention has been described in what is presently considered to be a preferred embodiment, many variations and modifications will become apparent to those skilled in the art. Accordingly, it is intended that the invention not be limited to the specific illustrative embodiment, but be interpreted within the full spirit and scope of the appended claims.

We claim as our invention:

1. A system for monitoring the condition of a heat exchange unit used in the operation of a vehicle, with the vehicle and the heat exchange unit being from a population of like vehicles and heat exchange units having passage for flow of a first fluid through said unit from an inlet to an outlet thereof, and passage for the flow of a second fluid through said unit from an inlet to an outlet thereof for cooling said first fluid, said system comprising:

(a) at least one sensor, positioned proximal to said heat exchange unit, for taking a plurality of temperature readings representative of a first temperature associated with either the first fluid or the second fluid toward a respective inlet of said unit and a second temperature associated with a respective fluid toward a respective outlet of said unit;

(b) a processor, in communication with the sensor, to which data representative of the temperatures is transmitted;

(c) a database, in communication with the processor, comprising data representative of at least one predetermined condemning limit for measures of effectiveness of a population of like heat exchange units and data representative of at least one operating parameter associated with the operation of the vehicle;

(d) said processor calculating a measure of effectiveness of said heat exchange unit based on said data representative of the first temperature and second temperature;

(e) a monitor for detecting a level of the operating parameter of the vehicle;

(f) said processor comparing the measure of effectiveness of said heat exchange unit at said level of the operating parameter with said predetermined condemning limit associated with the operating parameter for the vehicle, and generating a signal indicative of the condition of said heat exchange unit relative to a condition of the population of like heat exchange units.

2. The system of claim 1 wherein the processor adjusts the predetermined condemning limit associated with the measures of effectiveness of the population of like heat exchange units to reflect a difference between the operating parameter in the database and the detected operating parameters for said respective vehicle before the comparison of the measure of effectiveness of said heat exchanger unit with the predetermined condemning limit.

3. The system of claim 1 wherein the processor adjusts the measure of effectiveness of said heat exchange unit to reflect a difference between the detected operating parameter and the operating parameter in the database before the comparison of the measure of effectiveness of said heat exchange unit with the predetermined condemning limit.

4. The system of claim 2 wherein said operating parameter in the database comprises at least one ambient temperature in which the vehicle operates, at least one geographic location of the vehicle, an elevation of the vehicle or a time period within a calendar year within which the vehicle operates.

5. The system of claim 1 wherein said sensor is positioned in spaced relation to a plurality of discrete points along the heat exchange unit for taking said temperature readings along the surface of the heat exchange unit at said discrete points.

6. The system of claim 1 wherein said first temperature readings comprise an inlet temperature of said first fluid entering the unit and an outlet temperature of said first fluid exiting the unit.

7. The system of claim 1 wherein said plurality of temperatures detected include an inlet temperature of said second fluid entering the unit and an outlet temperature of said second fluid exiting the heat exchange unit.

8. The system of claim 7 wherein said at least one sensor comprises a portable infrared sensor held in spaced relation to each of said plurality of discrete points for taking the temperature readings.

9. The system of claim 7 wherein said temperature readings are taken of the surface of the heat exchange unit at said discrete points and said processor adjusts the temperature readings to represent temperatures of the first fluid or second fluid.

10. A system for monitoring the condition of a heat exchange unit used in the operation of a vehicle, with the vehicle and the heat exchange unit selected from a population of like vehicles and heat exchange units having passage for flow of a first fluid through said unit from an inlet to an outlet thereof, and passage for the flow of a second fluid through said unit from an inlet to an outlet thereof for cooling said first fluid, said system comprising:

(a) at least one sensor, positioned proximal to said heat exchange unit, for taking a plurality of temperature readings representative of a first temperature associated with either the first fluid or the second fluid toward a respective inlet of said unit and a second temperature associated with the respective fluid toward a respective outlet of said unit;

(b) a processor, in communication with the sensor, to which data representative of the temperatures is transmitted;

(c) at least one predetermined condemning limit associated with measures of effectiveness of the heat exchange units selected from a population of like heat exchange units;

(d) said processor calculating a measure of effectiveness of the heat exchange unit based on said data representative of the first temperature and the second temperature; and, (e) said processor comparing said measure of effectiveness to said least one predetermined condemning limit associated with the measures of effectiveness of the population of like heat exchange units, and generating a signal indicative of the condition of the heat exchange unit relative to the condition of the population of like heat exchange units.

11. The system of claim 10 wherein said predetermined condemning limit comprises a limit above which the measure of effectiveness of the heat exchange generates a signal indicative of a healthy condition of the heat exchange unit.

12. The system of claim 10 wherein said predetermined condemning limit comprises a limit below which the measure of effectiveness of the heat exchange generates a signal indicative of an unhealthy condition of the heat exchange unit.

13. The system of claim 10 further comprising a database that includes data representative of at least one operating parameter for the operation of the vehicle, and said at least one predetermined condemning limit is associated with said at least one operating parameter of the vehicle, and said system further comprises a monitor for detecting a level of said operating parameter of the vehicle, and said processor comparing the measure of effectiveness of said heat exchange unit at said level of the operating parameter with said predetermined condemning limit associated with the operating parameter for the vehicle, and generating a signal indicative of the condition of said heat exchange unit relative to condition of the population of like heat exchange units.

14. The system of claim 13 wherein said data representative of the operating parameter of the vehicle comprises at least one ambient temperature in which the vehicle operates, a geographic location of the vehicle, at least one elevation of the vehicle or at least one time period within a calendar year within which the vehicle operates.

15. The system of claim 10 wherein said temperature readings are taken to include an inlet temperature of said first fluid entering the unit, an outlet temperature of said first fluid exiting the unit and an outlet temperature of the second fluid exiting the unit.

16. The system of claim 10 wherein said temperature readings are taken to include an inlet temperature of said second fluid entering the unit, an outlet temperature of said second fluid exiting the heat exchange unit and an outlet temperature of the first fluid exiting the unit.

17. The system of claim 10 wherein said sensor is positioned in spaced relation to a plurality of discrete points along the heat exchange unit for taking said temperature readings along the surface of the heat exchange unit at said discrete points.

18. The system of claim 17 wherein said at least one sensor comprises a portable infrared sensor held at a predetermined spaced relation to each of said plurality of discrete points for taking the temperature readings.

19. The system of claim 17 wherein said temperature readings are taken of the surface of the heat exchange unit at said discrete points and said processor adjusts the temperature readings to represent temperatures of the first fluid or second fluid.

20. A method for monitoring the condition of a heat exchange unit for a vehicle, said heat exchange unit having a first fluid passing through said unit, and a second fluid passing through said unit for cooling said first fluid, the method comprising the steps of:

(a) positioning at least one sensor proximal to the heat exchanger unit;

(b) collecting data, using said sensor, that is indicative of a first temperature associated with either the first fluid or the second fluid toward a respective inlet of said unit and a second temperature associated with the respective fluid toward a respective outlet of said unit;

(c) calculating a measure of effectiveness of the operation of the heat exchange unit based on said first temperature and said second temperature;

(d) establishing at least one predetermined condemning limit for the measure effectiveness of the heat exchange unit determined from an analysis of measures of effectiveness of a population of like heat exchange units, and (e) generating a signal responsive to a comparison of the measure of effectiveness of the heat exchange unit with said predetermined condemning limit, with said signal being indicative of a condition of the heat exchange unit relative to a condition of the population of like heat exchange units.

21. The method of claim 20 further comprising the step of providing a database comprising data representative of predetermined condemning limits for measures of effectiveness of a population of like heat exchange units and data representative of at least one operating parameter associated with the operation of the vehicle, detecting a level of said operating parameter of the vehicle, and comparing the measure of effectiveness of said heat exchange unit at said level of the operating parameter with said predetermined condemning limit in the database associated with the operating parameter for the vehicle, and generating a signal indicative of the condition of said heat exchange unit relative to a condition of the population of like heat exchange units.

22. The method of claim 21 further comprising the step of adjusting the predetermined condemning limit relative to a difference between operating parameter limit associated with the predetermined condemning limit and the level of the operating parameter.

23. The method of claim 21 further comprising the step of adjusting the measure of effectiveness of the vehicle relative to a difference between operating parameter limit associated with the predetermined condemning limit and the level of the operating parameter.

24. "The method of claim 21 wherein said operating parameters are selected from data comprising:

an ambient temperature within which the vehicle operates, a geographic location of the vehicle, an elevation of the vehicle and a time period within a calendar year within which the vehicle operates.

25. The method of claim 20 wherein said predetermined condemning limit comprises a limit above which the measure of effectiveness of the heat exchange unit generates a signal indicative of a healthy condition of the heat exchange unit.

26. The method of claim 20 wherein said predetermined condemning limit comprises a limit below which the measure of effectiveness of the heat exchange unit generates a signal indicative of an unhealthy condition of the heat exchange unit.

* * * * *